United States Patent [19]

Kakumaru et al.

[11] Patent Number: 4,985,564

[45] Date of Patent: Jan. 15, 1991

[54] ACRIDINE COMPOUND AND PHOTOPOLYMERIZABLE COMPOSITION USING THE SAME

[75] Inventors: Hajime Kakumaru; Yoshitaka Minami, both of Hitachi; Naohiro Kubota; Shinya Mashimo, both of Urawa, all of Japan

[73] Assignees: Hitachi Chemical Co., Ltd.; Adeka Argus Chemical Co., Ltd., Tokyo, Japan

[21] Appl. No.: 401,794

[22] Filed: Sep. 1, 1989

[30] Foreign Application Priority Data

Sep. 3, 1988 [JP] Japan .................... 63-221138
Apr. 28, 1989 [JP] Japan .................... 1-111193

[51] Int. Cl.$^5$ .................................. C07D 219/14
[52] U.S. Cl. ............................. 546/104; 546/102; 430/287
[58] Field of Search ........................... 546/102, 104

[56] References Cited

U.S. PATENT DOCUMENTS 4,587,200  5/1989  Tamoto et al. .................. 430/281

FOREIGN PATENT DOCUMENTS

| 1027467 | 12/1971 | Fed. Rep. of Germany . |
|---|---|---|
| 47-4126 | 2/1972 | Japan . |
| 48-38403 | 11/1973 | Japan . |
| 49-11936 | 3/1974 | Japan . |
| 53-27605 | 8/1978 | Japan . |
| 59-226002 | 12/1984 | Japan . |
| 60-164739 | 8/1985 | Japan . |
| 1354541 | 5/1974 | United Kingdom . |

OTHER PUBLICATIONS

Patent Abstracts of Japan, vol. 10, No. 7 (P-419)(2064), Jan. 11, 86.
Chemical Abstracts, vol. 101, No. 7, Aug. 13, 1984, p. 404, Column 1, Abstract No. 54893r.
Chemical Abstracts, vol. 78, No. 15, Apr. 16, 1973, p. 463, Column 1, Abstract No. 97461r.
Yiyao Gongye 1984, (3), 8-11, (ch).

*Primary Examiner*—Nicholas S. Rizzo
*Attorney, Agent, or Firm*—Antonelli, Terry, Stout & Kraus

[57] ABSTRACT

Acridine compounds such as 1,4-butylene-bis-$\beta$-(acridin-9-yl)acrylate, or the like are high in light sensitivity and suitable as a photopolymerization initiator.

9 Claims, No Drawings

ACRIDINE COMPOUND AND PHOTOPOLYMERIZABLE COMPOSITION USING THE SAME

BACKGROUND OF THE INVENTION

This invention relates to an acridine compound, a photopolymerizable composition using the same as a photopolymerization initiator, a process for producing a resist image and a process for producing a printed circuit board, using the same.

Photopolymerizable compositions comprising an unsaturated monomer or an unsaturated prepolymer and a photopolymerization initiator are known to be polymerized by irradiation of light. These photopolymerizable compositions are used in a variety of fields such as printing plates for lithography, letterpress printing, intaglio printing, etc., photocurable inks, coating compositions, printed circuit substrates, adhesives, etc.

As the photopolymerization initiator, there have been proposed various compounds such as benzophenones, benzoins and the like aromatic ketones. But, these aromatic ketones have defects in that obtained polymers are colored and light irradiation for a long period of time is necessary due to their small effects. Thus, these aromatic ketones are unsatisfactory in practical use.

On the other hand, in order to increase light sensitivity, there are disclosed a combination of an aromatic ketone such as aminophenyl ketone and 2,4,5-triarylimidazole dimer (U.S. Ser. No. 731,733, Japanese Patent Examined Publication No. 48-38403), a combination of aminophenyl ketone and an active methylene compound or an amino compound (U.S. Serial No. 877,853, Japanese Patent Examined Publication No. 49-11936), an acridine or phenazine capable of including a fused benzol ring (Japanese Patent Examined Publication No. 53-27605), a 9-substituted acridine compound (Japanese Patent Unexamined Publication No. 47-4126), a combination of 9-phenylacridine and a thiol group-containing heterocyclic compound (Japanese Patent Unexamined Publication No. 59-226002), a substituted 9-benzoylacridine (Japanese Patent Unexamined Publication No. 60-164739), etc. But these compounds are insufficient to provide light sensitive photopolymerizable compositions.

SUMMARY OF THE INVENTION

It is an object of the present invention to provide an acridine compound effective as a photopolymerization initiator overcoming defects of prior art. It is another object of the present invention to provide a photopolymerizable composition using the acridine compound as a photopolymerization initiator.

The present invention provides an acridine compound of the formula:

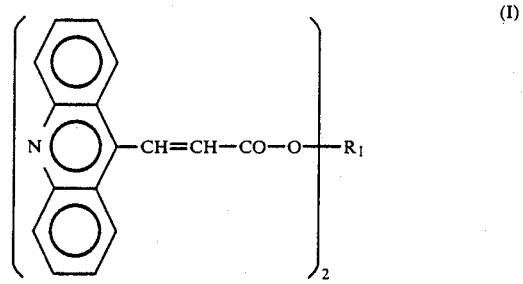

wherein $R_1$ is a hydrocarbon group having 2 to 20 carbon atoms or $-(R_2O)_nR_2-$; $R_2$ is an alkylene group having 2 to 4 carbon atoms; an n is an integer of 1 to 10.

The present invention also provides a photopolymerizable composition comprising a photopolymerizable unsaturated compound and an acridine compound of the formula (I) as a photopolymerization initiator. The photopolymerizable composition may further contain a thermoplastic organic polymer.

The present invention also provides a process for producing a resist image, and a process for producing a printed circuit board, using the photopolymerizable composition.

DESCRIPTION OF THE PREFERRED EMBODIMENTS

An acridine compound [a diester of $\beta$-(acridin9-yl) acrylic acid] of the formula:

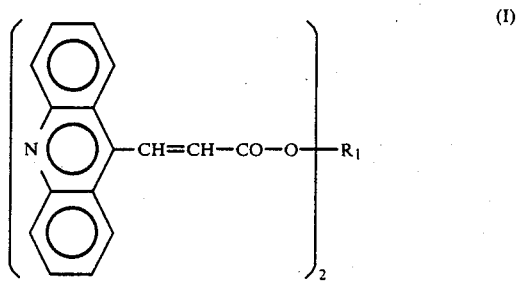

wherein $R_1$ is a hydrocarbon group having 2 to 20 carbon atoms or $-(R_2O)_nR_2-$; $R_2$ is an alkylene group having 2 to 4 carbon atoms; and n is an integer of 1 to 10, is remarkably effective as a photopolymerization initiator, can proceed the polymerization to the necessary degree by light irradiation in a short time, and gives no coloring to a polymer obtained. Further, the photopolymerizable composition containing the acridine compound of the formula (I) is excellent in storage stability and not changed in nature even if stored for a long period of time.

In the formula (I), the hydrocarbon group having 2 to 20 carbon atoms and represented by $R_1$ includes, for example, 1,2-ethylene, 1,2-propylene, 1,3-propylene, 2,2-dimethyl-1,3-propylene, 1,2-butylene, 1,4-butylene, hexamethylene, octamethylene, decamethylene, dodecamethylene, 1,4-cyclohexylene, p-cyclohexanedimethylene, p-benzenedimethylene, 4,4'-isopropylidenebis(cyclohexylene), p-phenylene, 4,4'-isopropylidenebis(phenylene), etc. The alkylene group having 2 to 4 carbon atoms and represented by $R_2$ includes, for example, 1,2-ethylene, 1,2-propylene, 1,3-propylene, 1,2-butylene, 1,4-butylene, etc.

Preferable examples of the acridine compound of the formula (I) are as follows.

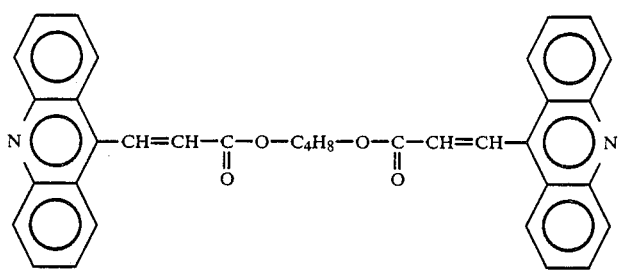

(II)

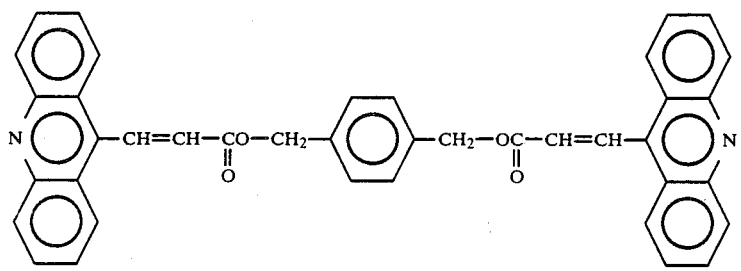

(III)

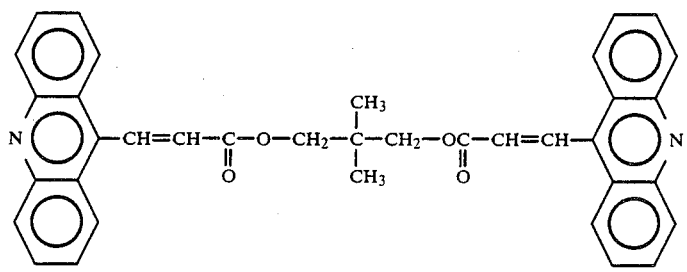

(IV)

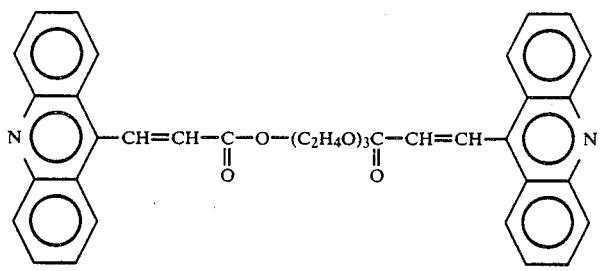

(V)

The acridine compound of the formula (I) can be produced by reacting, for example, β-(acridin-9-yl)acrylic acid or a reactive derivative thereof such as an alkali metal salt thereof or a monoester thereof, with a glycol of the formula:

wherein R₁ is as defined above, or a dihalogen compound of the formula:

wherein X is a halogen atom; and R₁ is as defined above, at a temperature of preferably 50° to 200° C.

β-(Acridin-9-yl)acrylic acid or an alkali metal salt thereof can be obtained by reacting 9-methylacridine with chloral to yield 9-(2-hydroxy-3,3,3-trichloropropyl)acridine, which is further reacted with a hydroxide of an alkali metal such as potassium hydroxide.

Typical examples of synthesis of the acridine compound of the formula (I) are as follows.

(A) Ester interchange reaction of β-(acridin-9-yl)acrylic acid and glycol

Glycol is dissolved in an inert solvent such as a lower alkyl-substituted aromatic solvent, e.g., toluene, xylene, pseudocumene, etc. Then, 1.0 to 1.5 equivalent weight of β-(acridin-9-yl)acrylic acid per equivalent wieght of glycol is mixed therewith, followed by addition of 0.01 to 1% by weight of tetraisopropyl titanate or dibutyl tin oxide as a catalyst based on the total weight of the acid and glycol. The reaction is carried out under a nitrogen stream at the reflux temperature of the solvent used, while removing by-produced water by distillation.

(B) Ester interchange reaction of β-(acridin-9-yl)-acrylic acid lower alkyl ester and glycol Glycol in an amount of 1 equivalent weight and 1.0 to 1.5 equivalent weight of β-(acridin-9-yl)acrylic acid methyl, ethyl or the like lower alkyl ester are dissolved in an inert solvent (e.g. an aromatic hydrocarbon). Then, tetraisopropyl titanate or dibutyl tin oxide as a catalyst in an amount of 0.01 to 1% by weight based on the total weight of the acid and glycol is added thereto. The reaction is carried out by heating at a temperature higher than the boiling point of a lower alcohol by-produced and lower than the boiling point of the solvent used, while removing the by-produced alcohol by distillation.

(C) Esterification of β-(acridin-9-yl)acrylic acid metal salt with alkylene dihalide An alkylene dichloride or dibromide is dissolved in a solvent such as an amide series solvent, e.g. N,N-dimethylformamide, N,N-dimethylacetamide, N-methylpyrrolidone, 1,3-dimethylimidazolinone, etc. or dimethylsulfoxide, etc. Then, 1.0 to 1.5 equivalent weight of β-(acridin-9-yl)acrylic acid alkali metal salt per equivalent weight of alkylene dihalide is added thereto to carry out the reaction at 60° to 150° C.

After washing the reaction solution with water in the cases of (A) and (B), or after filtering the reaction product for removing by-produced alkyl halide in the case of (C), the solvent is removed by distillation to give the desired compound as a viscous liquid or to give the desired compound as crystals from a suitable solvent.

β-(Acridin-9-yl)acrylic acid, an alkyl ester thereof and an amide compound thereof are disclosed in Yiyao Gongye vol. 3, pp. 8–11 (1984) in that these compounds are effective for remedy for Schistosomiasis japonica. But, said reference is quite silent on diesters of said carboxylic acid and does not describe nor suggest that these compounds are useful as a photosensitizer.

The acridine compound of the formula (I) is useful as a photopolymerization initiator for polymerizing unsaturated compound by light irradiation. Further, the acridine compound of the formula (I) is also effective as a photosensitizer, alone or as a mixture with one or more other known photosensitizers.

The present invention also provides a photopolymerizable composition comprising (A) 100 parts by weight of a compound having a boiling point of 100° C or higher under a normal pressure and at least one ethylenic unsaturated group, (B) 0 to 400 parts by weight of a thermoplastic organic polymer, and (C) 0.01 to 10 parts by weight of an acridine compound of the formula (I) as a photopolymerization initiator.

As the compound (A) having a boiling point of 100° C or higher under a normal pressure and at least one ethylenic unsaturated group, there can be used, for example, the following ones:

compounds obtained by adding an α,β-unsaturated carboxylic acid to a polyhydric alcohol, e.g. tetraethylene glycol di(meth)acrylate[(meth)acrylate meaning a methacrylate or acrylate; hereinafter used in this sense], polyethylene glycol di(meth)acrylate[the number of ethylene group being 2 to 14], trimethylolpropane di(meth)acrylate, trimethylolpropane tri(meth)acrylate, tetramethylolmethane tri(meth)acrylate, tetramethylolmethane tetra(meth)acrylate, polypropylene glycol di(meth)acrylate [the number of propylene group being 2 to 14], dipentaerythritol penta(meth)acrylate, dipentaerythritol hexa(meth)acrylate, etc.

Compounds obtained by adding an α,β-unsaturated carboxylic acid to a glycidyl group-containing compound, e.g. trimethylolpropane triglycidyl ether triacrylate, bisphenol A diglycidyl ether diacrylate, etc.

Esterified compounds obtained from a polycarboxylic acid such as phthalic anhydride, and a compound having both a hydroxyl group and an ethylenic unsaturated group, such as β-hydroxyethyl (meth)acrylate, etc.

Alkyl esters of acrylic acid or methacrylic acid such as methyl (meth)acrylate, ethyl (meth)acrylate, butyl (meth)acrylate, 2-ethylhexyl (meth)acrylate, etc.

Reaction products of a compound having at least one isocyanate group and a compound having at least one hydroxyl group and at least one vinyl group.

Examples of the compound having at least one isocyanate group are toluene diisocyanate, trimethylhexamethylene diisocyanate, diphenyl diisocyanate, diphenylmethane diisocyanate, 3,3′-dimethyl-4,4′-diphenyl diisocyanate, etc.

Examples of the compound having at least one hydroxyl group and at least one vinyl group are β-hydroxy (meth)acrylate, vinyl alcohol, trimethylolpropane diacrylate, tetramethylolmethane (meth)acrylate, diethylene glycol mono(meth)acrylate, etc.

Unsaturated compounds having at least on ethylenic double bond, said compound being able to be a monomer which is cured by addition polymerization with irradiation of actinic light to yield a substantially insoluble cured product, or a polymer having at least one ethylenic unsaturated double bond at side chains or a main chain:

Examples of the unsaturated compounds are unsaturated carboxylic acids such as acrylic acid, methacrylic acid, itaconic acid, crotonic acid, maleic acid, fumaric acid, etc.; esters obtained from these unsaturated carboxylic acids and mono- or polyhydric alcohols; amides obtained from these unsaturated carboxylic acids and mono- or polyvalent amines; polyhydroxy esters of (meth)acrylates [(meth)acrylate means a methacrylate or an acrylate] obtained from mono- or polyvalent carboxylic acids and polyhydric alcohols; unsaturated polyesters or unsaturated polyamides obtained from unsaturated dicarboxylic acids (and other dicarboxylic acids) and polyhydric alcohols or polyvalent amines; urethane acrylates obtained by the reaction of an urethane compound having a terminal isocyanate group obtained from a diisocyanate and a polyhydric alcohol, with hydroxyalkyl (meth)acrylate; epoxy acrylates obtained by the reaction of a bisphenol or a polyglycidyl ether of polyol with (meth)acrylic acid; linear polyesters obtained by the reaction of a dicarboxylic acid anhydride with glycidyl (meth)acrylate; di(meth)acrylic acid-modified polyesters or polyamides obtained by reacting a polyester or polyamide having carboxylic groups at two ends with glycidyl (meth)acrylate; etc.

Examples of the mono- or polyhydric alcohols in these unsaturated compounds are methanol, ethanol, propanol, butanol, allyl alcohol, octanol, N,N-dimethylethanol, ethylene glycol, diethylene glycol, triethylene glycol, propylene glycol, neopentyl glycol, 1,3-butanediol, 1,4-butanediol, 1,6-hexanediol, glycerine, trimethylolpropane, trimethylolethane, tris(2-hydroxyethyl) isocyanurate, pentaerythritol, diglycerine, ditrimethylolpropane, dipentaerythritol, etc.

Examples of mono- or polyvalent amines are ammonia, methylamine, butylamine, octylamine, diethylamine, dibutylamine, ethylenediamine, diethylenetriamine, morphodine, piperazine, 1,6-hexamethylenediamine, melamine, etc.

Examples of the polyvalent carboxylic acids other than the unsaturated dicarboxylic acids are phthalic acid, isophthalic acid, terephthalic acid, trimellitic acid, pyromellitic acid, tetrahydrophthalic acid, succinic acid, adipic acid, sebacic acid, etc.

Examples of the diisocyanates are toluene diisocyanate, diphenylmethane diisocyanate, hydrogenated diphenylmethane diisocyanate, isocyanatemethylcyclohexane isocyanate, hexamethylene diisocyanate, isophorone diisocyanate, etc.

Examples of the unsaturated carboxylic acid esters or amides among the unsaturated compounds are methyl acrylate, ethyl acrylate, butyl acrylate, isooctyl acrylate, 2-hydroxyethyl acrylate, 2-hydroxyethyl acrylate, N,N-dimethylaminoethyl acrylate, methyl methacrylate, ethyl methacrylate, ethylene glycol diacrylate, triethylene glycol diacrylate, 1,4-butanediol diacrylate, trimethylolpropane triacrylate, pentaerythritol triacrylate, pentaerythritol tetraacrylate, tris(2-acryloyloxyethyl) isocyanurate, dipentaerythritol tetrahexaacrylate, glycerine diacrylate, triethylene glycol dimethacrylate, trimethylolpropane trimethacrylate, pentaerythritol trimethacrylate, ethylene glycol dicrotonate, diallyl maleate, bis(acryloyloxyethoxyphenyl)-propane, acrylamide, methacrylamide, acrylmorpholide, ethylenebisacrylamide, hexamethylenebisacrylamide, methylenebismethacrylamide, etc.

Other photopolymerizable unsaturated compounds are diallyl phthallate, diallyl malonate, divinyl adipate, divinyl phthalate, vinyl acetate, isobutyl vinyl ether, ethylene glycol divinyl ether, styrene, acrylonitrile, triallyl isocyanurate, triallyl phosphate, etc.

As the component (B), that is, the thermoplastic organic polymer, there can be used copolymers of acrylic or methacrylic acid and an alkyl ester of acrylic or methacrylic acid, copolymers of acrylic or methacrylic acid alkyl ester, and/or acrylic or methacrylic acid, and a vinyl monomer copolymerizable therewith.

Examples of the alkyl ester of acrylic or methacrylic acid are methyl acrylate, methyl methacrylate, ethyl acrylate, ethyl methacrylate, butyl acrylate, butyl methacrylate, 2-ethylhexyl acrylate, 2-ethylhexyl methacrylate, etc.

Examples of the vinyl monomer copolymerizable with acrylic or methacrylic acid alkyl ester and acrylic or methacrylic acid are tetrahydrofurfuryl acrylate or methacrylate, dimethylethyl acrylate or methacrylate, diethyl acrylate or methacrylate, glycidyl methacrylate, 2,2,2-trifluoroethyl acrylate or methacrylate, 2,2,3,3-tetrafluoropropyl acrylate or methacrylate, acrylamide, diacetone(meth)acrylamide, styrene, vinyl toluene, methacrylamide, etc.

As the thermoplastic organic polymer, it is possible to use homopolymers of the above-mentioned compounds, copolyesters such as polyesters of terephthalic acid, isophthalic acid and sebacic acid, copolymers of butadiene and acrylonitrile, cellulose acetate, cellulose acetate butylate, methyl cellulose, ethyl cellulose, etc.

The thermoplastic organic polymer is used in an amount of 0 to 400 parts by weight, preferably 20 to 250 parts by weight per 100 parts by weight of the component (A). By the use of the thermoplastic organic polymer, film coating properties and film strength of the obtained cured product can be improved. When the amount is more than 400 parts by weight, the light sensitivity is lowered due to relatively small amounts of other components.

The weight average molecular weight of the thermoplastic organic polymer is preferably 10,000 or more from the viewpoints of film coating properties and film strength.

The component (C) is preferably used in an amount of 0.01 to 10 parts by weight, preferably 0.1 to 5 parts by weight, per 100 parts by weight of the component (A). When the amount is less than 0.01 part by weight, no sufficient light sensitivity can be obtained, resulting in insufficient progress of the photopolymerization. On the other hand, when the amount is more than 10 parts by weight, storage stability of the photopolymerizable composition is lowered not to be used practically.

The component (C), that is, the photopolymerization initiator can be used as a mixture of two or more compounds of the formula (I). Further, the component (C) may include one or more organic amines and organic sulfur compounds in order to increase the effect.

Examples of the organic amines are, for example, triethanolamine, triisopropanolamine, methyldiethanolamine, octyldiethanolamine, octadecyldiethanolamine, dibutylethanolamine, dioctylethanolamine, diethanolaniline, diethanolamine, methylethanolamine, butylethanolamine, tetrahydroxyethylethylenediamine, tetrahydroxyethylhexamethylenediamine, triethylamine, tributylamine, dimethylaminopropylamine, dimethylaniline, 4-dimethylaminotoluene, 4-diethylaminotoluene, 4-dimethylaminocyanobenzene, 4-diethylaminocyanobenzene, 4-dimethylaminobromobenzene, 4-diethylaminobromobenzene, 4-dimethylaminonitrobenzene, 4-diethylaminonitrobenzene, 4-diethylaminonitrobenzene, 4-dimethylaminobenzoic acid alkyl ester, 4-diethylaminobenzoic acid alkyl ester, 4-dimethylaminopyridine, 4-diethylaminopyridine, 4-pyrrolidinopyridine, phenylglycine, diethylaniline, diethylamine, dioctylamine, tetramethylethylenediamine, Michler's ketone, anthranilic acid, etc.

Examples of the suflur compounds are 2-mercaptoimidazole, 2-mercaptooxazole, 2-mercaptothiazole, 2-mercaptobenzimidazole, 2-mercaptobenzoxazole, 6-chloro-2-mercaptobenzimidazole, 5-methylmercapto-1-phenyltetrazole, 6-methoxy-2-mercaptobenzimidazole, 2-mercaptonaphthoimidazole, 2-mercaptonaphthooxazole, 3-mercapto-1,2,4-triazole, etc.

The photopolymerizable composition may further contain one or more conventional additives such as heat polymerization inhibitors, colorants, plasticizers, surface protective agents, smoothing agents, adhesion accelerating agent, talc, etc., depending on purposes.

Examples of the heat polymerization inhibitors are hydroquinone, p-methoxyphenol, pyrogallol, naphthylamine, phenothiazine, t-butylcatechol, catechol, 2,6-di-t-butyl-p-cresol, $\beta$-naphthol, t-butylhydroquinone, etc.

Examples of the colorants are carbon black; metal powders such as silver powder, copper powder, aluminum powder, etc.; extender pigments such as chrome yellow pigment, titanium white, talc, alumina, etc.; inorganic pigments such as Milori blue, chrome vermilion, etc.; organic pigments and dyes such as Hansa Yellow (Yellow 6, C.I. 11670), Vulcan Orange (Orange 16, C.I. 21160), Permanent Yellow (Yellow 16, C.I. 20040), Lake Red 4R (Red 3, C.I. 12120), Brilliant Carmine 6B (Red 57, C.I. 15850), Rhodamine 6G Lake (Red 81, C.I. 45160), Eosine, Phloxine, Victoria Blue Lake (Blue 2, C.I. 44045), Phthalocyanine Blue B (Blue 15, C.I. 74160), Phthalocyanine Green (Green 7, C.I. 74260), Quinacridone Red Bluish, Dioxazine Violet Bluish, Alkali Blue Toner, Methyl Violet (C.I. Name, Basic Violet 1), fuchsin, Auramine base, Crystal Violet (C.I. Name, Basic Violet 3), Victoria Blue B (C.I. Name, Basic blue 26), Malachite Green (C.I. Name, Basic Green 4), Methyl Orange, Acid Violet 5BN (C.I. Name, Acid Violet 17), etc. It is possible to add a combination of a halogen compound such as carbon tetrabromide and a leuco dye so as to make the color of portions exposed to light change.

The photopolymerizable composition can be used as a solution of photopolymerizable composition dissolved in a solvent, or a solventless solution of photopolymerizable composition obtained by dissolving the components (B) and (C) in the ethylenic unsaturated compound (A) without using a solvent.

As the solvent, there can be used acetone, methyl ethyl ketone, methyl isobutyl ketone, methyl Cellosolve, ethyl Cellosolve, chloroform, methylene chloride, methyl alcohol, ethyl alcohol, etc.

The solution or solventless solution of photopolymerizable composition can be directly coated on a substrate such as a copper plate, by using a roll coater, a curtain coater, or the like, or a printing, immersion, or the like method. The photopolymerizable composition solution can also be coated on a support such a film, and if a solvent is contained, after removing the solvent, the photopolymerizable composition on the support is applied to a substrate.

The photopolymerizable composition can be used as a photocurable coating composition, a photocurable ink, a photosensitive printing plate, a photoresist, a pressure-sensitive adhesive, etc.

In the case of using the photopolymerizable composition as a photoresist for printed wiring boards, the solution of the photopolymerizable composition is used by coating on a substrate such as a copper plate, removing the solvent, if contained, for drying, exposing to an actinic light and photocuring the resin component. It is also possible to use the solution of photopolymerizable composition on a polyethylene terephthalate film, removing the solvent, if contained, for drying, laminating resulting film on a substrate, and photocuring the composition.

As a light source of actinic light, it is possible to use a light source which emits a light with a wavelength of 300 to 450 nm, e.g., a carbon arc lamp, a high-pressure mercury lamp, a xenone lamp, a metal halide lamp, a tungsten lamp, an argon laser, a helium-cadmium laser, etc.

The photopolymerizable composition of the present invention can be laminated (or coated) on a laminate having a metal layer on a surface thereof, subjected to imagewise exposure to light, followed by development to form a resist image on the laminate. The resist image-formed laminate is subjected to etching, followed by peeling of the resist image to give a printed circuit board.

Alternatively, the resist image-formed laminate is subjected to plating of a metal, followed by etching using a metal layer obtained by plating after peeling of the resist image to give a printed circuit board.

As the laminate having a metal layer on a surface thereof, there can be used a copper-clad laminate, an aluminum foil-clad laminate, a nickel foil-clad laminate, etc.

As the imagewise exposure to light and the development, there can be used conventional methods.

In the development, either an alkaline aqueous solution or an organic solvent can be used. When a thermoplastic organic polymer having carboxyl groups is used, the development can be carried out by using an alkaline aqueous solution.

Examples of the alkaline aqueous solution are a 0,5 to 2.0% by weight aqueous solution of sodium carbonate, a 0.2 to 1.0% by weight aqueous solution of sodium hydroxide, 1,1,1-trichloroethane, etc.

As mentioned above, the photopolymerizable composition has high light sensitivity.

The present invention is illustrated by way of the following Examples, in which all parts and percents are by weight, unless otherwise specified.

EXAMPLE 1

Synthesis of 1,4-butylene-bis-$\beta$-(acridin-9-yl) acrylate [Compound of the formula (II)]

Potassium salt of $\beta$-(acridin-9-yl)acrylic acid in an amount of 54 g (0.188 mole) was dispersed in 200 g of N,N-dimethylformamide and 20 g (0.093 mole) of 1,4-dibromobutane was added thereto with stirring and heating. The reaction mixture became a uniform solution at about 80° C. After stirring at 100° C for 2 hours, the reaction solution was cooled to 50° C. After removing deposited potassium bromide, the reaction solution was cooled to 15° C to deposit the product. The product was filtered, washed with 50 ml of methanol, and dried under reduced pressure to yield 41.6 g of yellow powder having a melting point of 171 to 174° C (yield 81%).

The resulting product was identified as the titled compound by the following NMR analysis.

| NMR (CDCl$_3$ solution, TMS standard) | | |
|---|---|---|
| $\delta$ value: | 1.2–1.9 | (4H, m, —CH$_2$—) |
| | 4.2–4.5 | (4H, t, —O—CH$_2$—) |
| | 6.4 | (2H, d, J=17Hz, —CO—CH=CH—) |
| | 7.2–8.2 | (16H, m, aromatic hydrogen) |
| | 8.5 | (2H, d, J=17Hz, —CO—CH=CH—) |

Ultraviolet absorption spectrum of the resulting compound was as follows:

$\lambda_{max} = 362$ nm, $\epsilon = 1.82 \times 10^4$

EXAMPLE 2

Synthesis of p-xylylene-bis[$\beta$-(acridin-9-yl)-acrylate] [Compound of the formula (III)]

The process of Example 1 was repeated except for using p-xylylene bromide in place of 1,4-dibromobutane to yield a yellow powder of the titled compound having a melting point of 258° to 263° C.

| NMR (DMSO-d$^6$ solution, TMS standard) | | |
|---|---|---|
| $\delta$ value: | 5.2 | (4H, s, —CH$_2$— $\phi$ —CH$_2$—) |
| | 6.4 | (2H, d, J=17Hz, —CO—CH=CH—) |
| | 7.1–8.2 | (20H, m, aromatic hydrogen) |

-continued

| NMR (DMSO-d⁶ solution, TMS standard) | |
|---|---|
| 8.5 | (2H, d, J=17Hz, —CO—CH=CH—) |

Ultraviolet absorption spectrum of the resulting compound was as follows:

$\lambda_{max} = 362$ nm $\epsilon = 1.65 \times 10^4$

EXAMPLE 3

Synthesis of triethylene glycol bis[β-(acridin-9-yl)-acrylate] [Compound of the formula (V)]

To 13 g (0.05 mole) of methyl β-(acridin-9-yl)-acrylate, 3.0 g (0.02 mole) of triethylene glycol and 30 g of xylene, 0.2 ml of tetraisopropyl titanate was added with stirring. While removing produced methanol by distillation, the reaction was carried out at 140 to 141° C. for 6 hours with stirring. The reaction solution was cooled to 80° C and 30 ml of water was added thereto. After filtering a trace amount of insoluble materials, 40 ml of xylene was added to the reaction solution, followed by washing with water, drying and removal of the solvent.

The resulting reddish brown liquid was purified by using a silica gel column to yield a yellowish liquid product with high viscosity.

| NMR (CDCl₃ solution, HMDS standard) | |
|---|---|
| δ value: 3.6–3.8 | (8H, m, —CH₂—O—CH₂—) |
| 4.3–4.5 | (4H, m, —CO—O—CH₂—) |
| 6.3 | (2H, d, J=17Hz, —CO—CH=CH—) |
| 7.1–8.2 | (16H, m, aromatic hydrogen) |
| 8.2 | (2H, d, J=17Hz, —CO—CH=CH—) |

Ultraviolet absorption spectrum of the resulting compound was as follows:

$\lambda_{max} = 360$ nm $\epsilon = 1.48 \times 10^4$

EXAMPLE 4

The process of Example 3 was repeated except for using neopentyl glycol in place of triethylene glycol to yield neopentyl glycol bis [β-(acrydin9-yl)-acrylate] [Compound of the formula (IV)].

EXAMPLES 5 TO 8, COMPARATIVE EXAMPLE 1

| Urethane acrylate (m.w. 1500) (NK Ester U-1080, mfd. by Shinnakamura Chemical Co., Ltd.) | 80 parts |
|---|---|
| Trimethylolpropane triacrylate (NK Ester A-TMP, mfd. by Shinnakamura Chemical Co., Ltd.) | 20 |
| 2-Mercaptobenzothiazole | 0.12 |
| Acridine compound (shown in Table 1) | 0.12 |

The above-mentioned ingredients were sufficiently kneaded and coated uniformly on a glass plate in 20 μm thickness using a doctor knife. The glass plate was exposed to a light from a high-pressure mercury lamp of 50 mJ. The coating was subjected to a tensile test using a No. 2 dumbbell specimen specified in JIS K-7113 and STM-H-500 test machine (mfd. by Toyo Goldfin Co.). Curing state of the coating was examined by calculating a Young's modulus at 50% elongation.

The results are shown in Table 1.

TABLE 1

| Example No. | Acridine compound | Young's modulus (dyn/cm²) |
|---|---|---|
| Example 5 | Compound (II) | 640 |
| Example 6 | Compound (III) | 610 |
| Example 7 | Compound (IV) | 580 |
| Example 8 | Compound (V) | 630 |
| Comparative Example 1 | 9-Phenylacridine | 290 |

As is clear from the results of Table 1, the acridine compounds of the present invention have a greater effect as a photopolymerization initiator than a known photopolymerization initiator of 9-phenylacridine.

EXAMPLES 9 AND 10, COMPARATIVE EXAMPLE 2

Solution A was prepared by mixing 400 g of tetraethylene glycol diacrylate, 2 g of Malachite Green, 100 g of barium sulfate, 10 g of methyl alcohol and 30 g of dimethylformamide. In Solution A, a photopolymerization initiator as listed in Table 2 was dissolved to give a solution of photopolymerizable composition (Examples 9 and 10).

The resulting solution was coated on a copper plate using an applicator and dried at 100° C for 10 minutes in a hot-air drier. The thickness of the coated film was about 20 μm. Then, the copper plate was placed on a conveyer and passed at a speed of 3 m/min 20 cm below a 7 KW high-pressure mercury lamp. The number of passing was measured until curing (finger touch tack on the surface disappeared).

The results are shown in Table 2.

The less the number of passing becomes, the higher the photosensitivity.

For comparison, a composition using a known compound (benzophenone and Michler's keton, Comparative Example 2) was prepared and measured the passing time until curing in the same manner as mentioned above.

The results are also shown in Table 2.

TABLE 2

| | Example 9 | Example 10 | Comparative Example 2 |
|---|---|---|---|
| Solution A (g) | 100 | 100 | 100 |
| Compound (II) (g) | 0.5 | 0.5 | — |
| Methyl 4-diethyl-aminobenzoate (g) | — | 4 | — |
| Benzophenone (g) | — | — | 3 |
| Michler's ketone (g) | — | — | 0.1 |
| Passing time until curing | 2 | 1 | 4 |

As is clear from Table 2, the photopolymerizable compositions of the present invention are higher in light sensitivity than the composition outside the present invention.

EXAMPLES 11 TO 14, COMPARATIVE EXAMPLES 3 TO 5

Solution B was prepared by mixing 52 g of copolymer of methyl methacrylate/methacrylic acid/2-ethylhexyl acrylate (weight ratio 60/20/20, weight average molecular weight : about 80,000), 10 g of tetraethylene glycol diacrylate, 30 g of dimethacrylate of polyoxyethylene bisphenol A (P≈5):

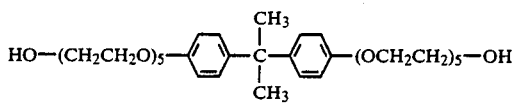

(BPE-10, a trade name, mfd. by Shinnakamura Chemical Co., Ltd.), 0.2 g of Malachite Green, 0.1 g of hydroquinone, 1.0 g of Leucocrystal Violet (leuco base of Crystal Violet, C.I. Name, Basic Violet 3), 0.5 g of carbon tetrabromide, 10 g of toluene, 130 g of methyl Cellosolve, 5 g of methyl alcohol and 10 g of chloroform (a total of non-volatile components 93.8 g). In Solution B, a photopolymerization initiator as listed in Table 3 was dissolved to give a photopolymerizable composition.

The resulting solution was uniformly coated on a polyethylene terephthalate film of 25 μm thick and dried in a hot-air circulating drier at 100° C for about 5 minutes to give a photopolymerization element. The film thickness of the photopolymerizable composition after dried was 25 μm.

On the other hand, copper surfaces of a copper-clad laminate obtained by laminating copper foils on both sides of glass-epoxy material (MCL-E-61, a trade name, mfd. by Hitachi Chemical Co., Ltd.) were polished with #800 sand paper, washed with water and dried in an air stream. The resulting copper clad laminate was heated to 60° C and subjected to lamination of the above-mentioned photopolymerization element on a copper surface while heating at 120° C.

The resulting substrate was exposed to light using a art work (photographic negative film) and a 3 KW high-pressure mercury lamp (Phenix-3000, mfd. by ORC Seisakusho, Ltd.) at 40 mJ/cm². The art work (photographic negative film) was made so as to lessen light transmitting amounts stepwise (step tablets increasing an optical density by 0.15 per every step, the first step being 0.05 in optical density) so as to evaluate the light sensitivity.

Then, the polyethylene terephthalate film was removed, followed by removal of unexposed portions by spraying an aqueous solution of 2% sodium carbonate at 30° C. for 50 seconds. Then, the step number of step tablets of photocured film formed on the copper-clad laminate was measured to evaluate the light sensitivity of the photopolymerizable composition.

The results are shown in Table 3. In Table 3, the larger the step number of step tablets becomes, the higher the light sensitivity becomes.

TABLE 3

| Example No. | Comparative Example | | | Example | | | |
|---|---|---|---|---|---|---|---|
| | 3 | 4 | 5 | 11 | 12 | 13 | 14 |
| Solution B (g) | 248.8 | 248.8 | 248.8 | 248.8 | 248.8 | 248.8 | 248.8 |
| Benzophenone (g) | 4 | 6 | 8 | — | — | — | — |
| Michler's ketone (g) | 0.2 | 0.2 | 0.2 | — | — | — | — |
| Compound (II) (g) | — | — | — | 0.7 | 1.0 | 0.7 | — |
| Compound (III) (g) | — | — | — | — | — | — | 0.7 |
| Methyl 4-diethylaminobenzoate (g) | — | — | — | — | — | 4 | — |
| Step number of step tablets | 3 | 4 | 4 | 8 | 10 | 10 | 8 |

As is clear from Table 4, the photopolymerizable compositions of the present invention show high light sensitivity.

As mentioned above, the acridine compounds and photopolymerizable compositions including the acridine compounds are suitably used in the fields which require high light sensitivity.

What is claimed is:

1. An acridine compound of the formula:

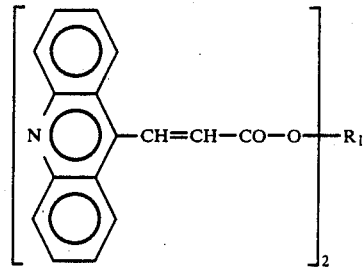

wherein $R_1$ is a hydrocarbon group selected from the group consisting of an alkylene group, a cycloalkylene group, an arylene group and an arylalkylene group having 2 to 20 carbon atoms or $(R_2O)_nR_2$—in which; $R_2$ is an alkylene group having 2 to 4 carbon atoms; and n is an integer of 1 to 10.

2. An acridine compound according to claim 1 wherein $R_1$ is a 1,4-butylene group.

3. An acridine compound according to claim 1, wherein $R_1$ is a p-xylylene group.

4. An acridine compound according to claim 1, wherein $R_1$ is a group of the formula:

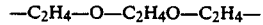

5. An acridine compound according to claim 1, wherein Ris a hydrocarbon group selected from the group consisting of 1,2-ethylene, 1,2-propylene, 1,3-propylene, 2,2-dimethyl-1,3-propylene, 1,2-butylene, 1,4-butylene, hexamethylene, octamethylene, decamethylene, dodecamethylene, 1,4-cyclohexylene, p-cyclohexanedimethylene, p-benzenedimethylene, 4,4'-isopropylidenebis(cyclohexylene), p-phenylene, and 4,4'-isopropylidenebis(phenylene) and $R_2$ is an alkylene group selected from the group consisting of 1,2-ethylene, 1,2-propylene, 1,3-propylene, 1,2-butylene and 1,4-butylene.

6. An acridine compound according to claim 1, which is

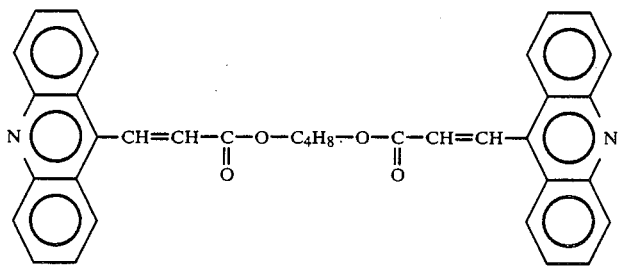
7. An acridine compound according to claim 1, which is
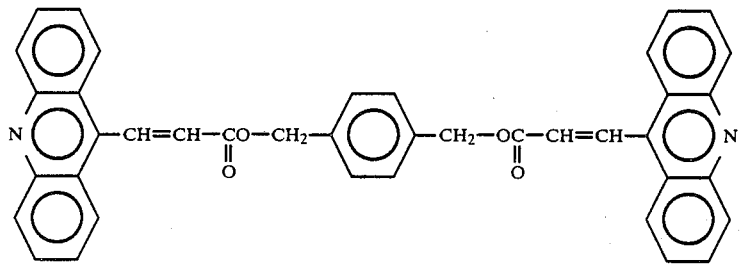
8. An acridine compound according to claim 1, which is
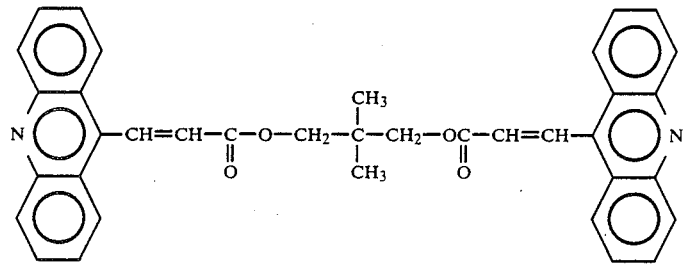
9. An acridine compound according to claim 1, which is
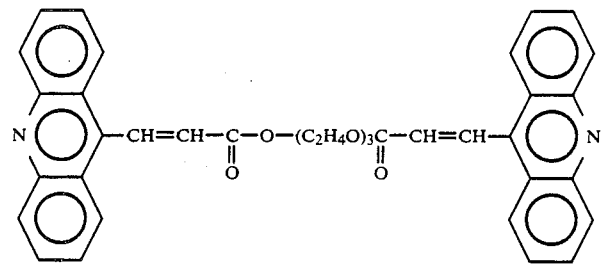
* * * * *